United States Patent
Kaluza et al.

Patent Number: 5,134,068
Date of Patent: Jul. 28, 1992

[54] TYPE II RESTRICTION ENDONUCLEAE MCRI

[75] Inventors: Klaus Kaluza, Bad Heilbrunn; Hans J. Hoeltke, Tutzing; Michael Jarsch, Bad Heilbrunn; Gudrun Schmitz-Agheguian, Bernried; Christoph Kessler, Dorfen, all of Fed. Rep. of Germany

[73] Assignee: Boehringer Mannheim GmbH, Mannheim, Fed. Rep. of Germany

[21] Appl. No.: 615,438

[22] Filed: Nov. 16, 1990

[30] Foreign Application Priority Data

Nov. 16, 1989 [DE] Fed. Rep. of Germany ....... 3938144

[51] Int. Cl.$^5$ .......................... C12N 9/22; C12P 19/34
[52] U.S. Cl. ........................................ 435/91; 435/199
[58] Field of Search .................................. 435/199, 91

[56] References Cited

PUBLICATIONS

Kessler, C., et al. (1985) Gene 33, 13.
Brensing-Kuppers, et al. (1990) FEBS Letts 264(2), 218–222.

*Primary Examiner*—Charles L. Patterson, Jr.
*Attorney, Agent, or Firm*—Felfe & Lynch

[57] ABSTRACT

Type II restriction endonuclease McrI is disclosed. This endonuclease has recognition sequence:

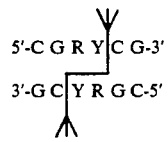

wherein R is G or A and Y is C or T, and the cleavage site indicated by the arrows. The endonuclease is preferably obtained from organism of genus Micrococcus. It can be used to recognize and cleave double stranded DNA sequence:

5'-CGRYCG-3' and its complementary sequence.

10 Claims, No Drawings

TYPE II RESTRICTION ENDONUCLEAE MCRI

TABLE 1

| DNA | Fragment lengths determined experimentally [bp] | Fragment lengths determined by computer analysis [bp] | Cleavage positions determined by computer analysis (at the base pairs) | Number of cleavage sites determined by computer analysis | Number of cleavage sites determined experimentally |
| --- | --- | --- | --- | --- | --- |
| SV 40 | | 0 | | 0 | |
| M13pm8 | 100, 2100, 2450, 2500 | 116, 2151, 2457, 2505 | 1421, 3878, 6383, 6499 | 4 | |
| phiX174 | 5380 | 5386 | 4601 | 1 | |
| pBR322 | 150, 280, 370, 420, 770, 920, 1500 | 149, 286, 367, 424, 765, 923, 1449 | 286, 653, 939 2388, 2812, 3735, 3884 | 7 | |
| pBR328 | 150, 280, 370, 400, 560, 780, 920, 1440 | 149, 286, 367, 395, 560, 784, 923, 1443 | 286, 653, 939, 1723, 2646, 2795, 4238, 4798 | 8 | | bp: base pair(s)

FIELD OF THE INVENTION

The invention concerns the type II restriction endonuclease McrI, a process for its isolation and its use.

BACKGROUND AND PRIOR ART

Type II restriction endonucleases are endodeoxyribonucleases which recognize and cleave particular DNA sequences. In this process one phosphodiester bridge is hydrolyzed in each polynucleotide strand of the target sequence. Type II restriction endonucleases are thus of value for the analysis of DNA molecules. Although type II restriction endonucleases are known which are specific for numerous DNA sequences, there is still a need for further restriction endonucleases with new specificities.

SUMMARY OF THE INVENTION

The present invention is a type II restriction endonuclease having the recognition sequence

5'-C G R Y C G-3'
3'-G C Y R G C-5' wherein R is A or G and Y is C or T,
and the cleavage site defined by the arrows.

DETAILED DESCRIPTION OF PREFERRED EMBODIMENTS

The new restriction endonuclease according to the present invention, which is denoted McrI hereafter, has a temperature optimum at ca. 37° C. The enzyme has good activity between pH 7.4 and pH 8.3 in 50 mmol/l Tris/HCl, 10 mmol/l (CH$_3$COO)$_2$Mg and 1.0 mmol/l DTE (dithioerythritol). The pH optimum is at ca. pH 7.8. An enzyme which has the same recognition sequence and cleavage site as McrI is not known.

The recognition sequence can be confirmed by the complete digestion of the DNA of the adeno 2 virus, of phage lambda and phage phiX174 and of the phage derivative M13mp8 and of the pBR322 and pBR328 plasmids. These DNA molecules are treated with McrI.

Table 1 shows a comparison of the cleavage site specificity observed with a cleavage site specificity determined by a computer for an enzyme which recognizes the following sequence:

5'-CGRYCG-3' wherein R is A or G and Y is C or T

The cleavage position within the recognition sequence of the enzyme can be determined on a M13 derivative having this recognition sequence at an interval of ca. 30-200 bases from the binding site of the universal sequencing primer (Messing, J. et al., (1981) Nucl. Acids Res. 9, 309–321). At first sequencing reactions according to the dideoxy chain-termination method (Sanger, F. et al., (1977) Proc. Natl. Acad. Sci. USA 74, 560–564, Messing, J. et al., (1981) Nucl. Acids Res. 9, 309–321) are carried out on the single-stranded DNA of the M13 derivate with the universal sequencing primer.

Parallel with this, the sequencing primer is radioactively labelled at the 5' end with T4-polynucleotide kinase and [γ-$^{32}$P]ATP. After hybridization of o this 5' end-labelled sequencing primer to the single-stranded M13 DNA, a partially double-stranded DNA is prepared in a "filling in" reaction with DNA-polymerase I (Klenow enzyme) and a deoxynucleotide triphosphate mixture of dATP, dCTP, dGTP and dTTP. An aliquot of this DNA, of which the newly synthesized strand is radioactively labelled at the 5' end is now cleaved with the restriction endonuclease McrI. Half of the cleavage preparation is additionally treated with T4-DNA polymerase in the presence of a mixture of all four deoxynucleotide triphosphates in order to obtain blunt DNA ends.

The analysis of the reaction products is carried out by electrophoresis on sequencing gels (8 mol/l urea, 5% polyacrylamide) and subsequent autoradiography. The results are interpreted according to Brown, N. L. and Smith, M. (Methods in Enzymology 65 (1980) 391–401). The position of the cleavage site is determined by a comparison of the distances of migration of the radioactively-labelled fragments with the sequencing ladder. The samples which were additionally treated with T4-DNA polymerase show a band which represents a migration distance shortened by two base pairs in comparison with the samples which were only cleaved with McrI. This therefore shows that McrI produces a 3' end which protrudes by two base pairs.

The cleavage of McrI has therefore the following specificity within the recognition sequence:

5'-C G R Y C G-3'

3'-G C Y R G C-5' wherein R is A or G and Y is C or T.

The number of cleavage sites determined experimentally is identical to the number of cleavage sites for the sequence

5'-C G R Y C G-3'

3'-G C Y R G C-5' wherein R is A or G and Y is C or T, obtained by computer analysis with the different DNA's (Table I). In addition these data were also compared with the tables in Gene 10 (1980) 357-370.

McrI is preferably isolated by culturing microorganisms of the genus Micrococcus, preferably microorganisms of the species *Micrococcus cryophilus* and isolating the enzyme from the cells. In particular, *Micrococcus cryophilus* DSM 20429 is preferred.

The microorganism *Micrococcus cryophilus* was deposited at the German Collection for Microorganisms, Gesellschaft für biotechnologische Forschung mbH, Mascheroder Weg 1b, 3300 Braunschweig, BRD and has the deposit number DSM 20429.

The microorganisms used for the isolation of the enzyme grow aerobically in Merck Standard I medium.

The optimal conditions for growth are at 18° C., pH 7.2-7.8. The doubling time is about two hours.

The usual biochemical methods of purification can be used for the isolation in which the presence of the enzyme in the respective fractions obtained can be easily tested on the basis of the cleavage of its recognition sequence. Lambda DNA is, for example, suitable as the substrate. The DNA fragments obtained are separated electrophoretically in agarose gels in buffer systems usually used for the fragment separation in the presence of ethidium bromide.

The enzyme is isolated and purified by the usual chemical and mechanical methods such as, for example, by high pressure dispersion, ultrasound or enzymatic lysis. The cells are preferably lysed by exposing them to high pressure of 5 bar. The cells are subsequently resuspended in Tris-HCl buffer, pH 8,0, containing protease inhibiters. Subsequently the cells are lysed by a French press. The further purification of the supernatant is preferably carried out by means of affinity chromatography and ion-exchange chromatography. Heparin-Sepharose ® CL-6B (Pharmacia) is for example suitable as the material for the affinity chromatography.

The product available under the name DEAE Sephadex ® (Pharmacia) is suitable as the anion-exchanger. Other chromatographic materials which are known to the expert are also suitable.

The following Examples elucidate the invention further.

EXAMPLE 1

*Micrococcus cryophilus* DSM 20429 is cultured at 18° C. for 25 hours and is harvested in the late logarithmic phase. The culture medium is Merck Standard I medium. The cell paste (30 g wet weight) is resuspended in 2.4 volumes buffer A (40 mmol/l Tris/HCl; pH 8.0; 0.1 mmol/l EDTA; 7 mmol/l 2-mercaptoethanol), which contains protease inhibitors. Subsequently, the cells are lysed by passing them twice through a French press at 23,000 lb/inch² and the precipitate is separated off. To the supernatant NH₄Cl is added (final concentration 0.6 mol/l). Nucleic acids are separated off by precipitation of polymin. After centrifugation the supernatant is treated with 55% ammonium sulfate. The precipitate is resuspended in buffer B.(40 mmol/l Tris/HCl; pH 8.0; 0.1 mmol/l EDTA; 7 mmol 2-mercaptoethanol; 10% (w/v) glycerol) and fractionated on a Q'sepharose column. A gradient of 0-0.5 mol/l NaCl is used for the elution McrI is found in the fractions between 0.2 and 0.3 mol/l NaCl. The active fractions are fractionated on a S Sepharose column. A gradient of 0-1 mol/l NaCl is used for the elution.

The active fractions, between 0.4 and 0.5 mol/l NaCl, are equilibrated against buffer B and applied to a heparin Sepharose column. A gradient of 0-0.1 mol/l NaCl in buffer B is used for the elution. McrI is found in the fractions between 0.4 and 0.6 mol/l NaCl.

The active fractions are pooled and dialyzed against storage buffer (20 mmol/l Tris-HCl, pH 8.0, 10 mmol/l 2-mercaptoethanol, 100 mmol/l NaCl, 0.1 mmol/l EDTA and 50% (v/v) glycerol).

EXAMPLE 2

Determination of the activity

Definition of the enzyme units: 1 U McrI cleaves 1 μg lambda DNA within 1 hour at 37° C. in 25 μl final volume.

17.9 μl water and 3.6 μl lambda DNA (optical density: 5.6 OD/ml) as well as 1 μl McrI solution (1 U/μl) are added to a mixture of 2.5 μl incubation buffer (500 mmol/l Tris-HCl, pH 7.5/37° C., 100 mmol/l magnesium acetate 1 mol/l NaCl and 10 mmol/l DTE). The solution is incubated for 1 hour at 37° C., cooled on ice and 5 μl of a terminating reagent consisting of 7 mmol/l urea, 20% (w/v) sucrose, 60 mmol/l EDTA and 0.01% (w/v) bromophenol blue is added. Subsequently separation is carried out by electrophoresis in 1% agarose gels for 3-4 hours at 100 V. The bands obtained are identified by comparison with a DNA length standard.

We claim:

1. Type II restriction endonuclease which recognizes and cleaves a DNA sequence at a position indicated by the arrows:

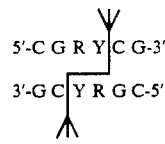

wherein R is G or A, and Y is C or T.

2. Restriction endonuclease of claim 1, obtained from microorganisms of the genus Micrococcus.

3. Restriction endonuclease of claim 1, obtained from *Micrococcus cryophilus* DSM 20429.

4. Restriction endonuclease of claim 1, characterized by a temperature optimum of about 37° C. and a pH optimum of about 7.8.

5. Process for the isolation of a type II restriction endonuclease of claim 1, comrising culturing a microorganism of genus Micrococcus which produces said restriction endonuclease under conditions favoring production thereof, and isolating said restriction endonuclease from said microorganism.

6. Process of claim 5, wherein said microorganism is *Micrococcus cryophilus* DSM 20429.

7. Process of claim 6, further comprising lysing cells of said microorganism to yield a supernatant and isolating said restriction endonuclease from said supernatant.

8. Process of claim 7, further comprising subjecting said supernatant to affinity chromatography, anion-exchange chromatography and cation-exchange chromatography to isolate said restriction endonuclease.

9. Process of claim 8, wherein said affinity chromatography is carried out using carrier bound heparin.

10. Method for obtaining a DNA sequence having terminal nucleotide sequence

5'-C G R Y-3'

3' G C and

5'-C G-3'

3'-Y R G C wherein R is A or G and Y is C or T, comprising contacting a DNA-containing sample with the restriction endonuclease of claim 1 and separating cleavage products produced thereby.

* * * * *